(12) United States Patent
Kavanagh et al.

(10) Patent No.: US 11,571,325 B2
(45) Date of Patent: *Feb. 7, 2023

(54) OSTOMY FACEPLATE INCLUDING INVERTIBLE STOMA COLLAR

(71) Applicant: Hollister Incorporated, Libertyville, IL (US)

(72) Inventors: Seamus T. Kavanagh, Libertyville, IL (US); Brock E. Masters, Des Plaines, IL (US); Mark W. Jockel, Chicago, IL (US); Christina Augustyn, Chicago, IL (US); Ronald S. Botten, Ballina (IE); Zubair A. Khan, Hoffman Estates, IL (US)

(73) Assignee: Hollister Incorporated, Libertyville, IL (US)

(*) Notice: Subject to any disclaimer, the term of this patent is extended or adjusted under 35 U.S.C. 154(b) by 467 days.

This patent is subject to a terminal disclaimer.

(21) Appl. No.: 16/663,026

(22) Filed: Oct. 24, 2019

(65) Prior Publication Data
US 2020/0093632 A1 Mar. 26, 2020

Related U.S. Application Data

(62) Division of application No. 15/103,186, filed as application No. PCT/US2015/013237 on Jan. 28, 2015, now Pat. No. 10,512,562.
(Continued)

(51) Int. Cl.
*A61F 5/443* (2006.01)
*A61F 5/448* (2006.01)
(Continued)

(52) U.S. Cl.
CPC ............. *A61F 5/443* (2013.01); *A61F 5/448* (2013.01); *A61F 5/449* (2013.01); *A61F 2005/4483* (2013.01)

(58) Field of Classification Search
CPC .......... A61F 5/443; A61F 5/448; A61F 5/449; A61F 2005/4483
See application file for complete search history.

(56) References Cited

U.S. PATENT DOCUMENTS 2,684,676 A * 7/1954 Perry ...................... A61F 5/445
604/344
3,021,843 A * 2/1962 Perry ...................... A61F 5/445
604/339
(Continued)

FOREIGN PATENT DOCUMENTS

EP 1348412 A1 10/2003
GB 2041753 A 9/1980
(Continued)

OTHER PUBLICATIONS

International Preliminary Report on Patentability issued by ISA/EPO in connection with PCT/US2015/013237 dated Aug. 2, 2016.

*Primary Examiner* — Guy K Townsend
(74) *Attorney, Agent, or Firm* — Levenfeld Pearlstein, LLC (57) ABSTRACT

A faceplate assembly for an ostomy pouch system including an invertible stoma collar is provided. The invertible stoma collar protrudes toward a stoma and defines an inlet opening. The invertible stoma collar is formed from a flexible material having an elastic memory, such that the stoma collar hugs the stoma as the stoma is received through the inlet opening, and becomes inverted. The inverted stoma collar has a tendency to regain its original shape, and thus, applies sufficient pressure to seal around the stoma without strangulating the stoma.

12 Claims, 5 Drawing Sheets

Related U.S. Application Data (60) Provisional application No. 61/932,572, filed on Jan. 28, 2014.

(51) Int. Cl.
  *A61F 5/449* (2006.01)
  *A61F 5/44* (2006.01)

(56) References Cited

U.S. PATENT DOCUMENTS

| | | | |
|---|---|---|---|
| 3,495,592 A * | 2/1970 | Shepard | A61F 5/445 604/338 |
| 3,780,739 A | 12/1973 | Frank | |
| 3,878,847 A * | 4/1975 | Marsan | A61F 5/445 604/338 |
| 4,095,599 A * | 6/1978 | Simonet-Haibe | A61F 5/445 604/336 |
| 4,219,023 A * | 8/1980 | Galindo | A61F 5/445 604/344 |
| 4,419,100 A * | 12/1983 | Alexander | A61F 5/448 604/339 |
| 4,610,676 A * | 9/1986 | Schneider | A61F 5/448 604/339 |
| 4,826,496 A * | 5/1989 | Ferguson | A61F 5/448 604/339 |
| 5,160,330 A * | 11/1992 | Cross | A61F 5/443 604/338 |
| 5,163,930 A | 11/1992 | Blum | |
| 5,185,008 A * | 2/1993 | Lavender | A61F 5/448 604/338 |
| 5,312,381 A * | 5/1994 | Brooks | A61F 5/448 604/338 |
| 5,346,482 A * | 9/1994 | Metz | A61F 5/448 604/338 |
| 5,492,943 A | 2/1996 | Stempel | |
| 5,501,677 A * | 3/1996 | Jensen | A61F 5/448 604/338 |
| 5,607,413 A * | 3/1997 | Holmberg | A61F 5/448 604/338 |
| 5,730,735 A * | 3/1998 | Holmberg | A61F 5/448 604/338 |
| 5,738,661 A | 4/1998 | Larice | |
| 6,071,268 A * | 6/2000 | Wagner | A61F 5/445 604/338 |
| 6,106,507 A * | 8/2000 | Botten | A61F 5/448 604/338 |
| 6,520,943 B1 * | 2/2003 | Wagner | A61F 5/445 604/338 |
| 6,723,079 B2 | 4/2004 | Cline | |
| 6,740,067 B2 | 5/2004 | Leise, Jr. | |
| 7,029,464 B2 | 4/2006 | Fenton | |
| 7,087,042 B2 * | 8/2006 | Montgomery | A61F 5/445 604/277 |
| 7,192,420 B2 * | 3/2007 | Whiteford | A61F 5/448 604/339 |
| 8,211,073 B2 * | 7/2012 | Dove | A61F 5/445 604/338 |
| 8,449,513 B2 * | 5/2013 | Abrams | A61F 5/445 604/342 |
| 9,402,761 B2 * | 8/2016 | Argent | A61F 5/445 |
| 9,517,158 B2 * | 12/2016 | Masters | A61F 5/448 |
| 9,707,120 B2 * | 7/2017 | Nguyen-DeMary | A61F 5/441 |
| 10,512,562 B2 * | 12/2019 | Kavanagh | A61F 5/449 |
| 2004/0039357 A1 * | 2/2004 | Andersen | A61F 5/448 604/332 |
| 2007/0027434 A1 * | 2/2007 | Pedersen | A61F 5/441 604/338 |
| 2010/0114044 A1 | 5/2010 | Cramer | |
| 2010/0241092 A1 * | 9/2010 | Nguyen-DeMary | A61F 5/4407 604/336 |
| 2011/0040269 A1 | 2/2011 | Cline | |
| 2011/0092929 A1 | 4/2011 | Weig | |
| 2011/0218507 A1 | 9/2011 | Andersen | |
| 2012/0059341 A1 * | 3/2012 | Masters | A61F 5/448 604/339 |
| 2012/0136324 A1 | 5/2012 | Hanuka et al. | |
| 2012/0165767 A1 * | 6/2012 | Abrams | A61F 5/445 604/338 |
| 2015/0297389 A1 * | 10/2015 | Nyberg | A61F 5/443 604/344 |
| 2016/0302959 A1 * | 10/2016 | Kavanagh | A61F 5/443 |

FOREIGN PATENT DOCUMENTS

| | | |
|---|---|---|
| GB | 2465742 A | 6/2010 |
| WO | 9960959 A1 | 12/1999 |
| WO | 0215827 A1 | 2/2002 |
| WO | 2005048891 A1 | 6/2005 |
| WO | 2005048892 A2 | 6/2005 |
| WO | 2011050816 A1 | 5/2011 |

* cited by examiner

OSTOMY FACEPLATE INCLUDING INVERTIBLE STOMA COLLAR

CROSS-REFERENCE TO RELATED APPLICATIONS

This is a divisional application of U.S. application Ser. No. 15/103,186, filed Jun. 9, 2016 which is a national stage application of International Patent Application No. PCT/US2015/013237, filed Jan. 28, 2015, which claims the benefit of and priority to U.S. Provisional Application No. 61/932,572, filed Jan. 28, 2014, the contents of which are incorporated fully by reference herein.

BACKGROUND

The present disclosure relates to a faceplate for ostomy appliances, and more particularly to a faceplate assembly including a stoma collar.

An ostomy appliance or system is a medical device or prosthetic that provides a means for collecting waste from a stoma typically created as a result of a surgical procedure to divert a portion of the colon or small intestine. One type of ostomy appliance is a pouch that is attached to a user around the stoma or the peristomal area.

Two common types of ostomy pouch systems are available, a one-piece pouch system and a two-piece pouch system. In a one-piece pouch system, a pouch is permanently attached to a faceplate, which also includes a skin barrier on its opposite surface for attaching the pouch system to a user. The skin barrier is typically formed from a sealing material that can provide a seal between the user's skin and the pouch system. Thus, in such a one-piece pouch system, the entire pouch system including the faceplate and the skin barrier must be removed from the user when a user wants to replace a pouch.

A two-piece pouch system also includes a faceplate and a pouch. However, the pouch and the faceplate are two separate assemblies, and are not permanently attached to each other. Instead, a two-piece pouch system includes a pair of coupling rings, one of which is fixedly attached to a faceplate assembly, while the other is attached to a pouch assembly. The coupling rings are configured to mate with each other, such that the pouch assembly can be securely and removeably attached to the faceplate assembly by engaging the coupling rings together. In use, the faceplate assembly is first attached to a user via a skin barrier, and the pouch assembly is secured to the faceplate by engaging the coupling rings together. Thus, a two-piece pouch system allows a user to remove and replace a pouch without removing the faceplate that is adhered to the user's skin. This can help to reduce the discomfort and irritation associated with removing skin barrier adhesive or gel from the user's skin.

The faceplate includes an inlet opening to receive a stoma. Leakage of stoma effluent can weaken the seal between a skin barrier and the user's skin, and can irritate the peristomal skin and cause infection. Peristomal skin irritation and infection can be very difficult to cure. Thus, efforts have been made to provide a faceplate that can fit and seal around a stoma to reduce the risk of stoma effluent coming in contact with a skin barrier or user's skin. However, an effective seal around a stoma remains as an area for further developments. The present disclosure provides a faceplate assembly according to various embodiments to provide improved seal around a stoma to reduce the risk of stoma effluent coming in contact with a skin barrier or user's skin.

BRIEF SUMMARY

A faceplate assembly including an invertible stoma collar for sealing around a stoma is provided according to various embodiments. In an initial state, the invertible stoma collar may be configured to protrude toward a stoma when the faceplate assembly is positioned proximate the stoma for attachment to a user. As the stoma is received through an inlet opening of the faceplate assembly, the stoma collar may hug the stoma and move with the stoma and become inverted. The stoma collar may be formed from a flexible material having an elastic memory, such that when inverted, the stoma collar may apply sufficient pressure around the stoma to seal around the stoma without strangulating.

Alternatively, the stoma collar may be formed from skin barrier material which is designed to be durable and resistant to liquid discharge.

Preferably, the faceplate assembly may have a convexity to facilitate raising recessed or flushed stomas. For example, the faceplate assembly may include a convex insert which can push against peristomal area to raise a recessed or flushed stoma.

In one aspect, an ostomy pouch system including a pouch and a faceplate assembly is provided. The faceplate assembly may include a faceplate, a skin barrier, a stoma collar, and an inlet opening for receiving the stoma. The stoma collar may protrude from the faceplate assembly, and may be configured to be inverted as the stoma is received through the inlet opening. The faceplate assembly may have a convex contour.

In one embodiment, the ostomy pouch system may be a two-piece ostomy pouch system including a pouch assembly and a faceplate assembly. The pouch assembly may include a pouch and a first coupling ring attached on the pouch. The faceplate assembly may include a second coupling ring, in which the first coupling ring and the second coupling ring are configured to engage together to attach the pouch assembly to the faceplate assembly. The faceplate assembly may also include a convex insert. The convex insert may include a first surface having a convexity and a second surface. The convex insert may be attached to the faceplate. The stoma collar may be arranged between the faceplate and the convex insert. Further, the stoma collar may include a collar portion that protrudes from faceplate assembly, in which the convexity of the convex insert and the collar protrude in a same direction toward the stoma when the faceplate assembly is positioned proximate the stoma for attachment to a user.

In one embodiment, the convex insert may include an inner convex portion, a base, and an inner wall defined by the inner convex portion. The stoma collar may include a collar and a convex base. The inner convex portion of the convex insert and the convex base of the stoma collar may be configured to have a same convex contour, such that the convex base may sit on the inner convex portion. The faceplate and the skin barrier may be disposed over the convex base, such that the convex base is sandwiched between the inner convex portion and the faceplate. In such an embodiment, the inner convex portion defines the convexity of the faceplate assembly. The second coupling ring may be attached to the second surface of the convex insert. The stoma collar may also include an annular tab formed on an inner surface about an intersection between the collar and the convex base. In such an embodiment, the annular tab may butt against the inner wall of the convex insert when the stoma collar is arranged on the convex insert.

In another embodiment, the ostomy pouch system may be a one-piece ostomy pouch system, in which the pouch is directly and permanently attached on the faceplate assembly. The stoma collar may include a collar and a base, in which the base may be arranged between the skin barrier and the faceplate. The faceplate assembly may also include a convex insert with an inlet opening formed therein. In such an embodiment, the collar and the convex insert may protrude in a same direction toward the stoma when the ostomy pouch system is positioned proximate the stoma for attachment to a user.

In any of the above discussed embodiments, the stoma collar may be formed from a flexible material having an elastic memory, such that when the stoma is received through an inlet opening defined by the stoma collar, the stoma collar hugs the stoma and becomes inverted as the stoma enters through the inlet opening of the faceplate. The inverted stoma collar may apply sufficient pressure around the stoma to seal against stoma effluent without strangulating the stoma. In one embodiment, the stoma collar may be formed from silicone.

In another aspect, a convex insert ring for attaching an ostomy pouch to a peristomal skin surrounding a stoma is provided. The convex insert ring may include a proximal bodyside surface having a convexity and an invertible stoma collar. The invertible stoma collar and the proximal bodyside surface of the convex insert ring may be configured to protrude in a same direction toward the stoma when the convex insert ring is positioned proximate the stoma for attachment to a user. The convex insert ring may include a convex insert including an inner convex portion, a base, and an inner wall defined by the inner convex portion. The invertible stoma collar may include a collar and a convex base. The inner convex portion of the convex insert and the convex base of the invertible stoma collar may have a same convex contour, such that the convex base may sit on the inner convex portion. A skin barrier adhesive layer may be disposed over the convex base, such that the convex base is sandwiched between the inner convex portion and the skin barrier adhesive layer, in which the inner convex portion defines a convexity of the faceplate assembly.

The stoma collar may also include an annular tab formed on its inner surface about an intersection between the collar and the convex base. In such an embodiment, the stoma collar may be arranged on the convex insert such that the annular tab butts against the inner wall of the convex insert. The stoma collar may be formed from a flexible material having an elastic memory, such that when the stoma is received through an inlet opening, the stoma collar hugs the stoma and becomes inverted. The inverted stoma collar may apply sufficient pressure around the stoma to seal around the stoma without strangulating the stoma. In one embodiment, the stoma collar is formed from silicone or other suitable flexible materials.

Other aspects, objectives and advantages will become more apparent from the following detailed description when taken in conjunction with the accompanying drawings.

BRIEF DESCRIPTION OF THE SEVERAL VIEWS OF THE DRAWINGS

The benefits and advantages of the present embodiments will become more readily apparent to those of ordinary skill in the relevant art after reviewing the following detailed description and accompanying drawings, wherein.

DETAILED DESCRIPTION

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Figure 1:
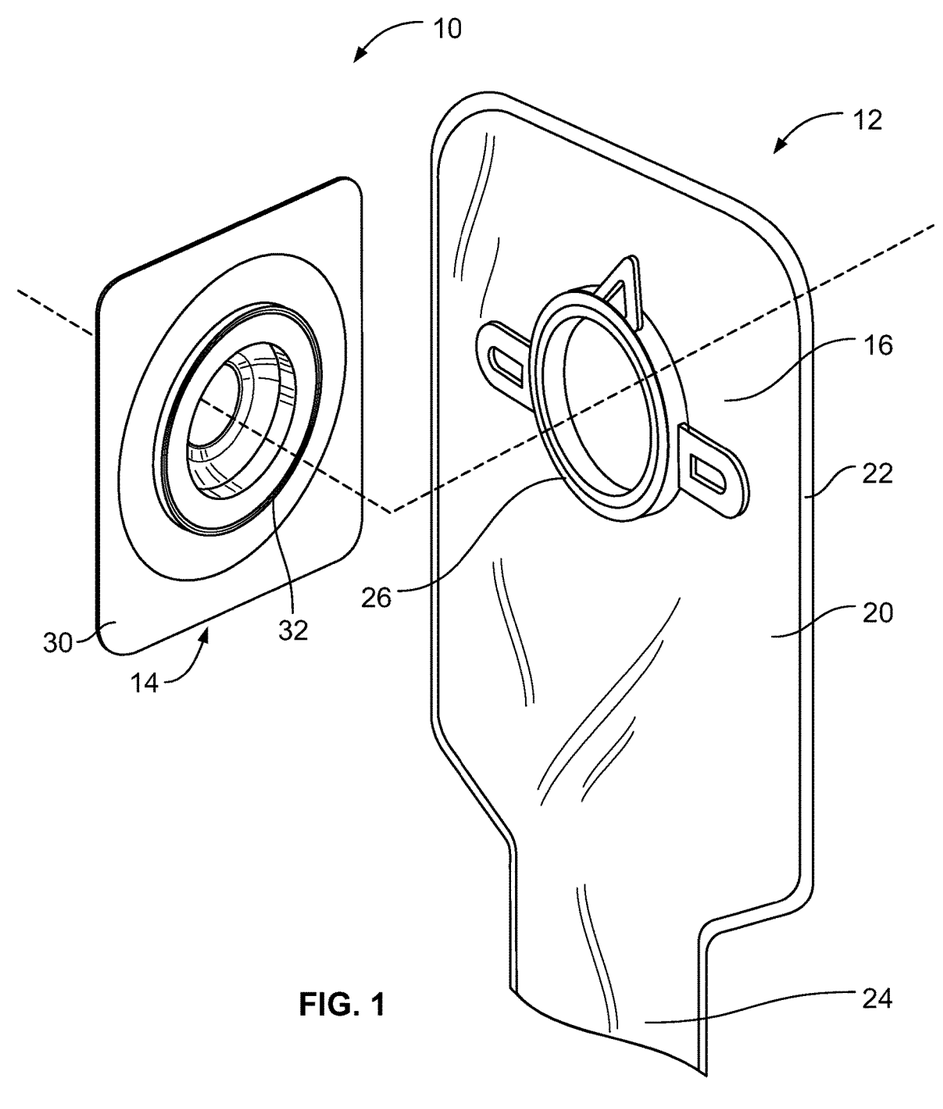
FIG. 1 is a perspective illustration of a two-piece ostomy pouch system including a pouch assembly, and a faceplate assembly including an invertible stoma collar according to an embodiment.
Figure 2:
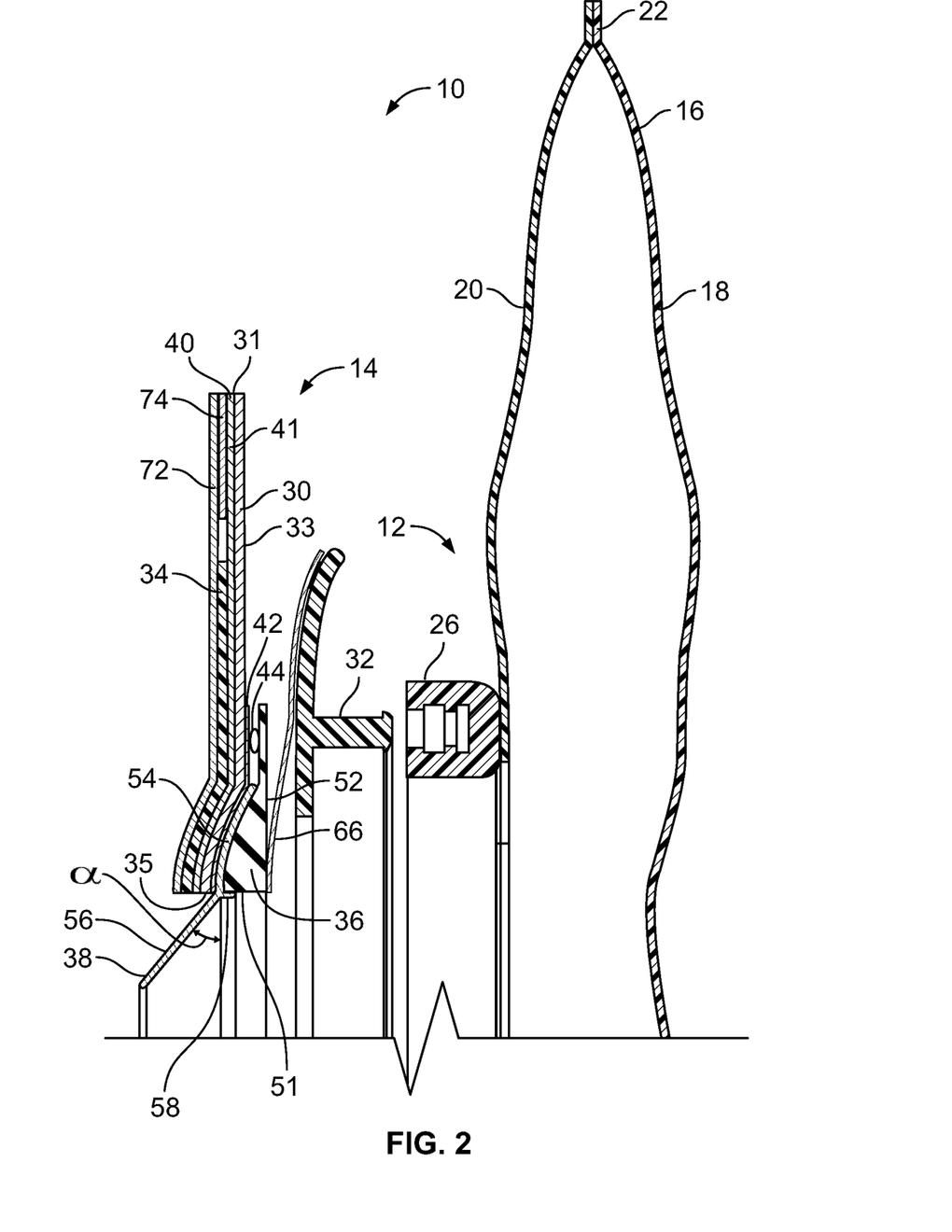
FIG. 2 is a partial sectional view of the two-piece ostomy pouch system of FIG. 1.

Referring to FIG. 1, an embodiment of a two-piece ostomy pouch system 10 is shown. FIG. 2 is a partial sectional view of the two-piece ostomy pouch system 10. The two-piece ostomy system 10 may include a pouch assembly 12 and a faceplate assembly 14. The pouch assembly 12 may include a collection pouch 16, which may be formed from two panels 18, 20. The panels 18, 20 may be sealed together around their periphery 22. The pouch 16 may include an open neck portion 24 at the pouch's lower end, which may be provided with closure means, such as a suitable clamp for maintaining the pouch in a closed condition. In another embodiment, the neck portion 24 may be omitted entirely and the panels 18, 20 may be sealed around the full periphery of the pouch 16. The pouch assembly 12 may also include a first coupling ring 26, which may be secured to the bodyside wall 20 of the pouch 16 by heat sealing or any other suitable means.

Figure 3:
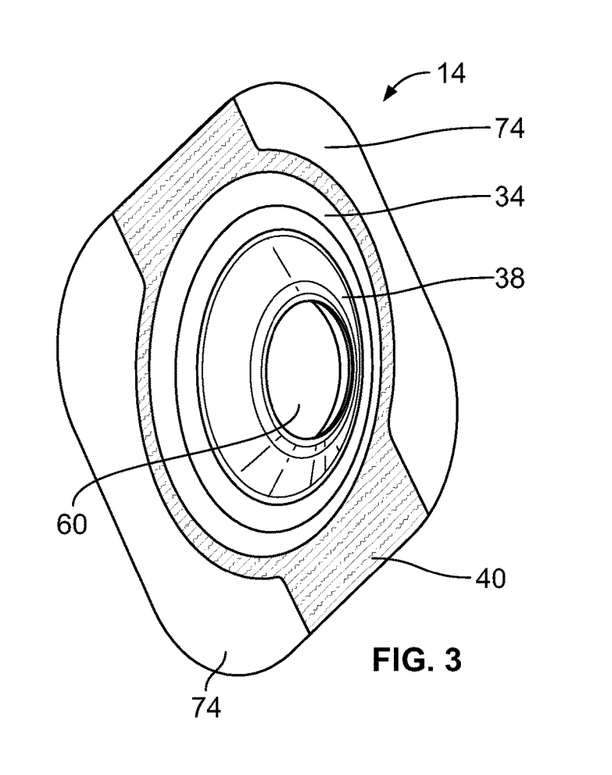
FIG. 3 is a perspective top view of the faceplate assembly including an invertible stoma collar of FIG. 1.

FIG. 3 is a top perspective view of the faceplate assembly 14. As shown in FIGS. 1-3, the faceplate assembly 14 may generally include a faceplate 30, a second coupling ring 32, a skin barrier 34, a convex insert 36, and a stoma collar 38. The faceplate assembly 14 may also include release liner layers 72, 74. Thicknesses of the layers of the faceplate assembly 14 in FIG. 2 are exaggerated and are not proportional.

The skin barrier 34 for attaching the faceplate assembly 14 to a user may be disposed over a first surface 31 of the faceplate 30. The skin barrier 34 may be formed from a suitable pliable and tacky material capable of sealingly engaging the peristomal area. Such barrier materials are well known in the art. For example, the skin barrier 34 may be formed from a medical-grade pressure sensitive adhesive that can adhesively secure the faceplate assembly 14 to a patient's skin in the peristomal region.

The faceplate 30 may include a layer formed from a gas-permeable, water-resistant microporous material. Preferably, the faceplate 30 is highly flexible, so that it will conform readily to body contours and body movements, and relatively strong and durable.

An adhesive layer 40 may be provided on the first surface 31 of the faceplate 30. In such an embodiment, the skin barrier 34 may be disposed on the adhesive layer 40 over the faceplate 30. The adhesive layer 40 may attach outer portions 41 of the faceplate 30 extending beyond the skin barrier 34 to the user's skin. Since the adhesive layer 40 may be in contact with the user's skin, the adhesive layer 40 is preferably formed using a skin contact grade adhesive, such as a medical-grade pressure sensitive adhesive.

A first release liner 72 may be provided over the skin barrier 34 and the adhesive layer 40. Further, second release liners 74 may be provided to cover at least some portions of the adhesive layer 40 that are disposed on the outer portions 41 of the faceplate 30, as shown in FIGS. 2 and 3. In such an embodiment, a user can grasp the portions covered with the second release liner 74 when handing the faceplate assembly 14 after removing the first release liner 72 to arrange the faceplate assembly 14 over a stoma.

In the embodiment shown, a backing film 42 may be provided on a second surface 33 of the faceplate 30 proximate an inner peripheral edge 35. The backing film 42 may be attached to the faceplate 30 via an adhesive, heat sealing, or other known sealing methods. The backing film 42 is optional and may be formed from a polymeric material having good heat sealing properties to facilitate sealing the faceplate 30 to the convex insert 36 or the second coupling ring 32. In the embodiment shown in FIG. 2, the faceplate 30 is attached to the convex insert 36 via an adhesive 44 between the backing film 42 and the convex insert 36. In other embodiments, the faceplate 30 may be attached to the convex insert 36 by sealing the backing film 42 to the convex insert 36 by heat sealing or other known sealing methods.

Figure 4:
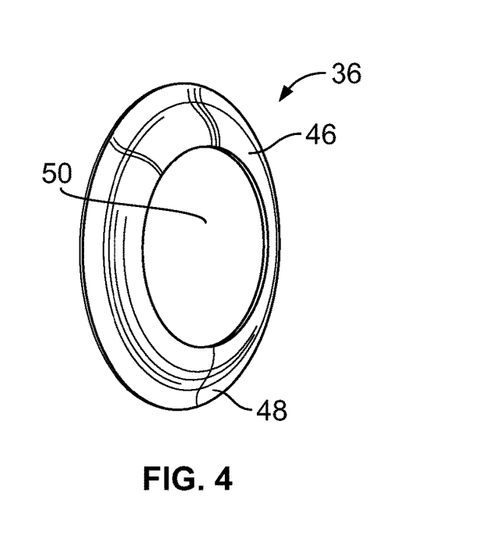
FIG. 4 is a perspective top view of a convex insert of the faceplate assembly according to an embodiment.

FIG. 4 is a perspective illustration of the convex insert 36. The convex insert 36 may include a convex inner portion 46 and a generally planar base 48. The convex insert 36 also includes an inlet opening 50 defined by the convex inner portion 46. As shown in FIG. 2, the convex insert 36 may have a generally flat bottom surface 52.

Figure 5:
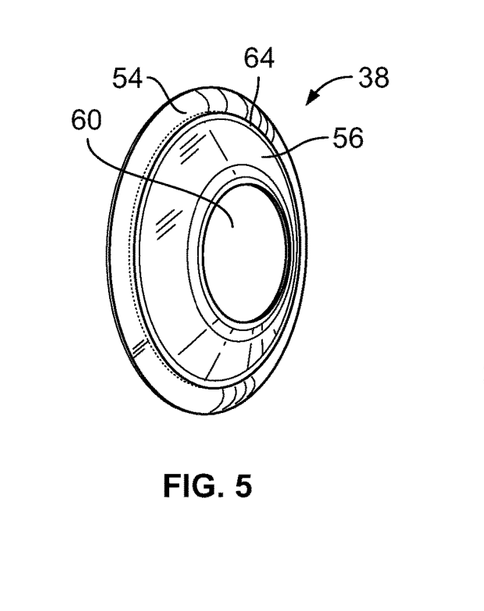
FIG. 5 is a perspective top view of the invertible stoma collar of the faceplate assembly according to an embodiment.
Figure 6:
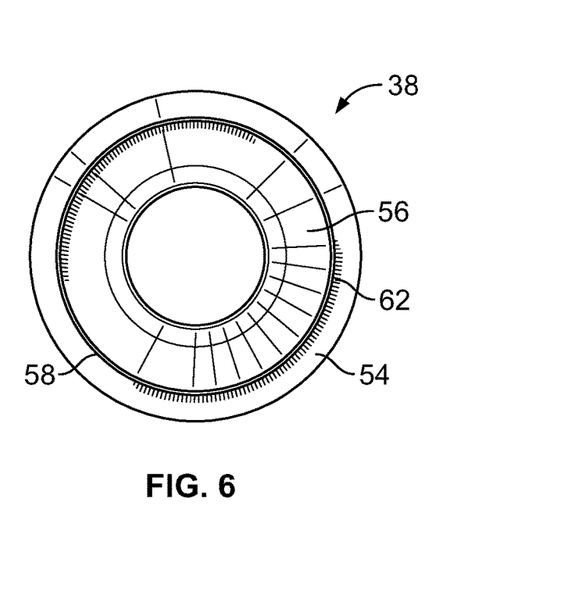
FIG. 6 is a perspective bottom view of a stoma collar of FIG. 5.

The stoma collar 38 may be arranged between the faceplate 30 and the convex insert 36. In the embodiment shown in FIG. 2, the stoma collar 38 is arranged adjacent the backing film 42 and the convex insert 36. FIG. 5 is a perspective top view of the stoma collar 38, and FIG. 6 is a perspective bottom view of the stoma collar 38. The stoma collar 38 may include a base 54, a collar 56, and an inlet opening 60 defined by the collar 56. The base 54 may be formed to have the same convex contour of the convex inner portion 46 of the convex insert 36, such that the base 54 may sit snuggly on the convex inner portion 46 as shown in FIG. 2. The collar 56 may protrude at an angle α from an intersection 64. The stoma collar 38 may also include an annular tab 58 formed about the intersection 64 between the base 54 and the collar 56 on the inner surface 62 of the stoma collar 38. The annular tab 58 may facilitate positioning of the stoma collar 38 on the convex insert 36, such that the intersection 64 of the stoma collar 38 is generally aligned over the inlet opening 50 of the convex insert 36. In positioning the stoma collar 38 on the convex insert 36, the base 54 of the stoma collar 38 is arranged on the convex inner portion 46 of the convex insert 36, such that the annular tab 58 is arranged in the inlet opening 50 of the convex insert 36, butting against an inner wall 51 of the convex insert 36 as shown in FIG. 2. In such an arrangement, the annular tab 58 facilitates accurate positioning of the stoma collar 38 on the convex insert 36, such that only the base 54 of the stoma collar 38 is sandwiched between the convex insert 36 and the faceplate 30, and the collar 56 protrudes from the faceplate assembly 14.

In the embodiment shown in FIG. 2, the stoma collar 38 is secured in place by the base 54 being sandwiched between the convex insert 36 and the faceplate 30 without other securing means, such as an adhesive or other sealing methods. However, in other embodiments, the base 54 of the stoma collar 38 may be adhesively attached or sealed to the convex insert 38 or the faceplate 30 or the backing film 42 via heat sealing or other known sealing methods.

In some embodiments, a stoma collar and a convex insert may be integrally formed as a single device. In other embodiments, a stoma collar 38 may be configured to be used as a separate device without a convex insert. For example, the stoma collar 38 may be provided as an accessory for use with a flat faceplate assemblies/skin barrier.

The stoma collar 38 may be formed using a soft and flexible material, such that when a stoma is received through the inlet opening 60 of the stoma collar 38, the collar 56 may move with the stoma and become inverted. Further, suitable materials for the stoma collar 38 may also have an elastic memory, such that the inverted stoma collar has a tendency to regain its original shape, to thereby apply slight but sufficient pressure around the stoma to seal against stoma output coming in contact with the peristomal skin without strangulating the stoma. Suitable materials for the stoma collar 38 include, but are not limited to, silicone, rubber, and elastomers.

As noted above, alternatively, the stoma collar may be formed from skin barrier material which is designed to be durable and resistant to liquid discharge.

For example, the stoma collar may be formed from an extended wear skin barrier material consisting essentially of a substantially homogeneous mixture on a percent weight basis of an elastomer blend essentially composed of about 2 percent to about 15 percent of one or more high molecular weight polyisobutylenes and about 5 percent to about 20 percent of one or more styrene block copolymers, said one or more polyisobutylenes of said blend being only of a viscosity average molecular weight within the range of about 750,000 to about 2,350,000; about 6 percent to about 20 percent of hydrocarbon plasticizer selected from the group consisting of petrolatum and mineral oil; about 10 percent to about 35 percent tackifier; up to about 1 percent antioxidant; and about 35 percent to about 65 percent water-absorbing hydrocolloids selected from the group consisting of sodium carboxymethylcellulose, pectin, and mixtures thereof, and optionally including minor amounts of other hydrocolloid gums. Examples of suitable extended wear skin barrier materials are set forth in Stempel, U.S. Pat. No. 5,492,943, the entirety of which is hereby incorporated by reference herein, and which is commonly owned by the assignee of the present application.

One example of such a skin barrier material is "Example (1)" in the table as excerpted below from the aforementioned patent (with listed ingredients specified on a weight percent basis):

|  | Examples | | | | | |
| --- | --- | --- | --- | --- | --- | --- |
|  | (1) | (2) | (3) | (4) | (5) | (6) |
| High MW polyisobutylene (Vistanex MM-L100) | 3.6 | 3.6 | 5 | 5 | 3.6 | 5 |
| Styrene-isoprene-styrene copolymer (Kraton 1107) | 8.4 | 8.4 | 8 | 5 | 8.4 | 5 |
| Petrolatum | 9.9 | 9.9 | 14.9 | 9.9 | — | 14.9 |
| Mineral Oil | — | — | — | — | 9.9 | — |
| Tackifier (Piccotac 95) | 24 | 36 | 18 | 25 | 24 | 20 |
| Antioxidant (Irganox 1010) | 0.1 | 0.1 | 0.1 | 0.1 | 0.1 | 0.1 |
| Sodium carboxymethyl-cellulose | 19 | 19 | 18 | 20 | 19 | 20 |
| Pectin | 35 | 23 | 18 | 35 | 35 | 35 |
| Gelatin | — | — | 18 | — | — | — |

The stoma collar 38 may also be formed from an adhesive formulated for adhering to moist tissue. Such an adhesive may comprise a silicone elastomer, a hydrophilic component, and a superabsorbent polymer. For example, a suitable adhesive may be formulated with an addition-curing two component silicone elastomer, a crosslinked polyacrylic acid polymer, and a sodium polyacrylate based superabsorbent polymer. The stoma collar 38 formed using such an adhesive can adhere to and seal around stoma outer walls, and move with the stoma during use to accommodate peristalsis movement.

In one embodiment, the stoma collar 38 may comprise a first layer formed from a first material and a second layer formed from a second material, in which the first material has a higher elastic memory than the second material. For example, the stoma collar 38 may include a first layer formed from a silicone, rubber, or elastomer, and a second layer formed from an adhesive for moist tissue. In such an embodiment, the first layer provides a sufficient elastic memory, such that the stoma collar 38 may provide slight pressure around a stoma without strangulating the stoma, while the second layer adheres to the stoma outer walls to improve sealing around the stoma.

Referring back to FIGS. 1 and 2, the second coupling ring 32 may be mounted on the bottom surface 52 of the convex insert 36. In the embodiment shown in FIG. 2, the second coupling ring 32 is mounted to the convex insert 36 by a connecting film 66, which is sealed to both the convex insert 36 and the second coupling ring 32. The connecting film 66 serves as an extension piece between the convex insert 36 and the second coupling ring 32. This allows the coupling ring 32 to be accessed slightly farther away from the rest of the faceplate assembly 14 and the user's skin. Such a configuration can increase access to the peristomal area to grasp the coupling ring 32 when attaching or removing the pouch assembly 12. The first coupling ring 26 and the second coupling ring 32 are configured to mate with each other, such that the pouch assembly 12 may be mechanically secured to the faceplate assembly 14 when the coupling rings 26, 32 are engaged together.

Figure 7:
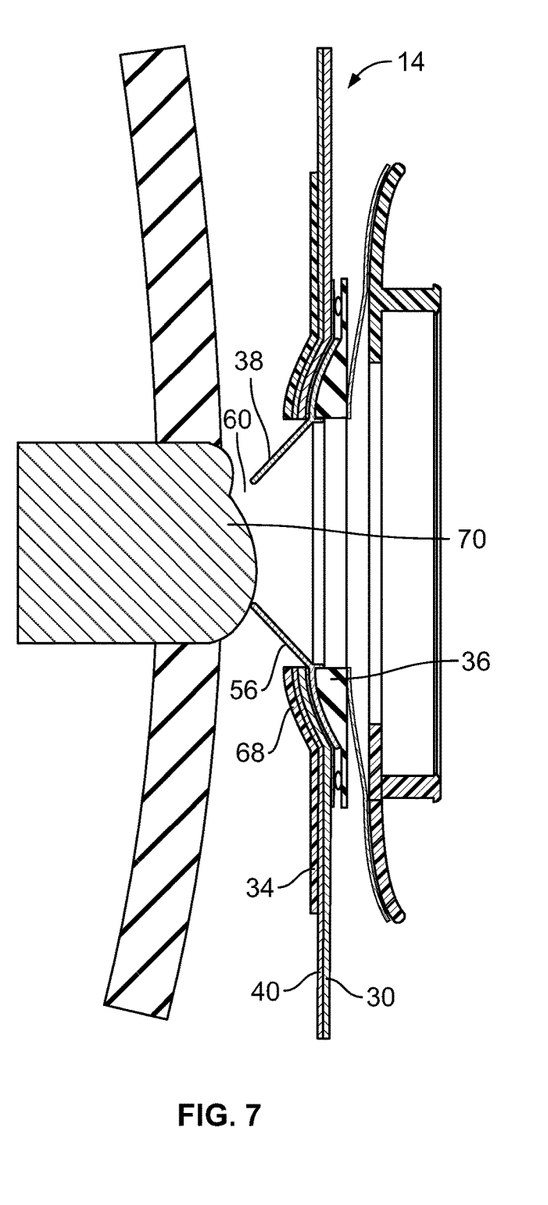
FIG. 7 is an illustration of the faceplate assembly positioned proximate a user's stoma, wherein the invertible stoma collar protrudes toward the stoma.
Figure 8:
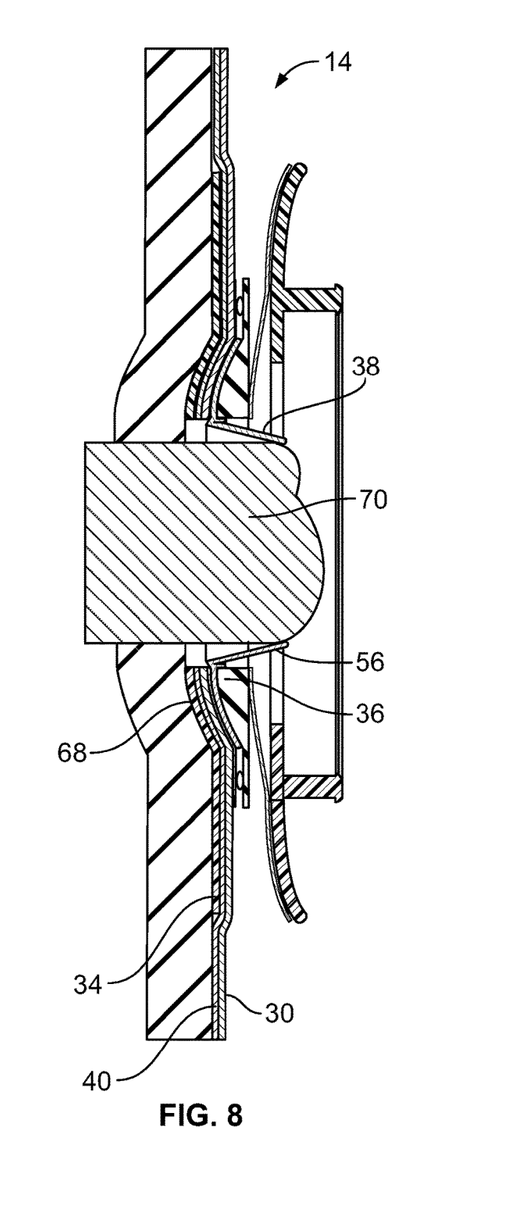
FIG. 8 is an illustration of the faceplate assembly with the stoma received through an inlet opening, in which the stoma collar is inverted and hugging the stoma.

In use, the faceplate assembly 14 is positioned proximate a stoma 70, such that the inlet opening 60 of the stoma collar 38 is placed over the stoma 70, as shown in FIG. 7. The collar 56 is configured to protrude from the faceplate assembly 14 toward the stoma 70. Then, the faceplate assembly 14 is pushed toward the user, such that the stoma 70 is received through the inlet opening 60. As the stoma 70 enters through the inlet opening 60, the collar 56 hugs the stoma 70 and moves with the stoma 70 and becomes inverted, such that the collar 56 now protrudes away from the user, as shown in FIG. 8. The collar 56, which is formed from a flexible material having an elastic memory, such as silicone, when inverted, has a tendency to regain its original shape. Thus, in its inverted state, the collar 56 may apply slight but sufficient pressure around the stoma 70 to seal against stoma output coming in contact with the peristomal skin without strangulating the stoma. The flexible collar 56 may also move with the stoma 70 during use and provide a continuous seal around the stoma 70. In the embodiment shown, the faceplate assembly 14 has a convex contour 68 defined by the convex insert 36. The convex contour 68 of the faceplate assembly 14 may facilitate raising a recessed or flush stoma when the convex faceplate assembly 14 is pushed against the peristomal skin.

Figures 9, 10:
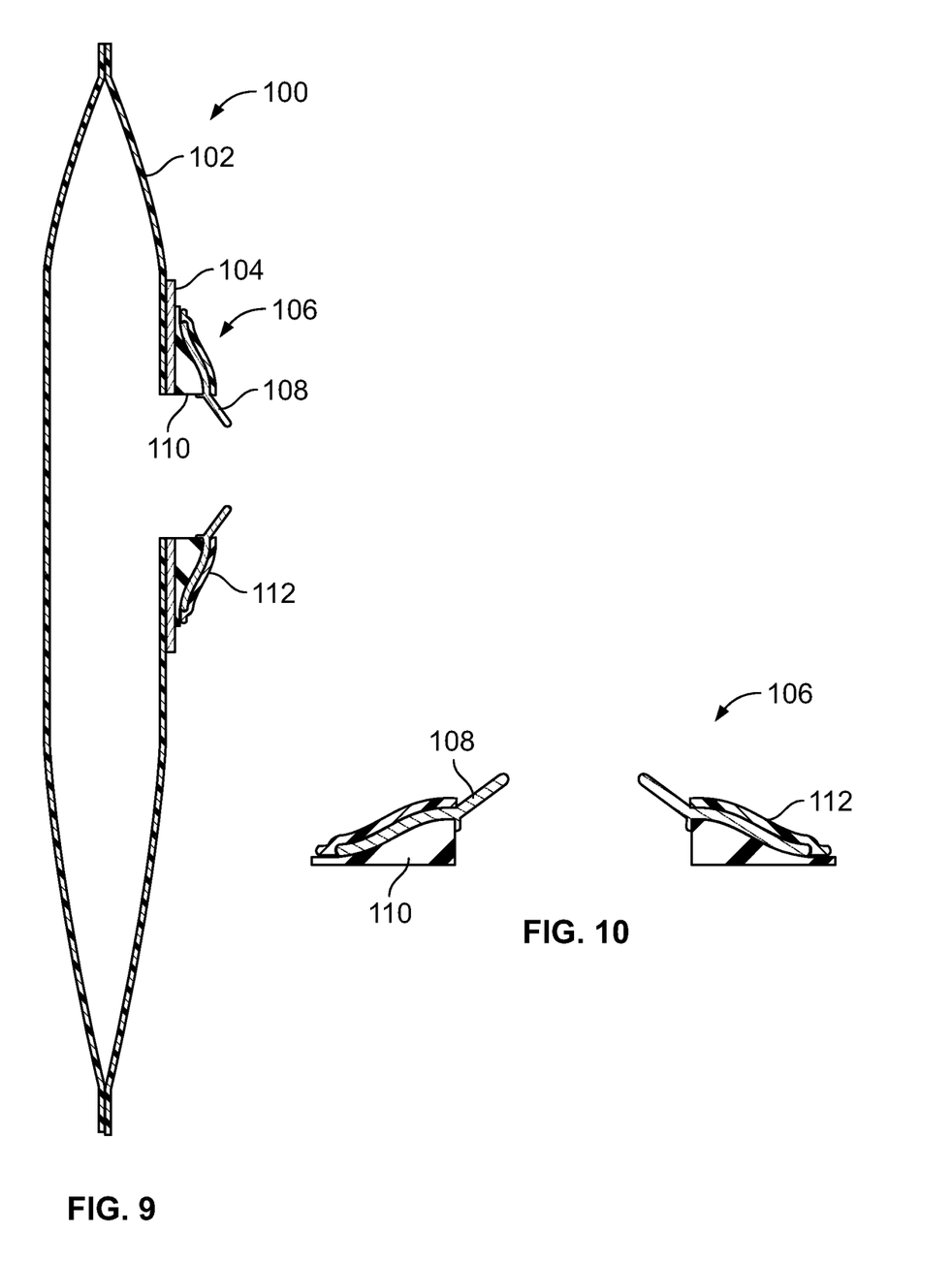
FIG. 9 is a sectional view of a one-piece ostomy pouch system including a convex insert with an invertible stoma collar according to an embodiment.
FIG. 10 is a sectional view of the convex insert including an invertible stoma collar of FIG. 9

FIG. 9 is a cross-sectional illustration of a one-piece ostomy pouch system according to an embodiment. The one-piece ostomy pouch system 100 may include a pouch 102, a faceplate 104, and a convex insert ring 106 including an invertible stoma collar 108. FIG. 10 is a cross-sectional illustration of the convex insert ring 106. The convex insert ring 106 may include a convex insert 110, the invertible stoma collar 108, and a skin barrier adhesive layer 112. The convex insert 110 and the invertible stoma collar 108 may be configured similar to the convex insert 36 and the stoma collar 38 of the previously discussed embodiments, such that the invertible stoma collar 108 sits snuggly on the convex insert 110. The convex insert ring 106 may be secured on the faceplate 104, as shown in FIG. 9, via an adhesive, heat sealing, or other known sealing methods.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. An ostomy pouch system, comprising:
   a pouch; and
   a faceplate assembly including a faceplate, a skin barrier, an invertible stoma collar, and an inlet opening for receiving stoma;
   wherein the stoma collar is configured to protrude from the faceplate assembly toward a stoma when the faceplate assembly is positioned proximate the stoma for attachment to a user and configured to be inverted as the stoma is received through the inlet opening.

2. The ostomy pouch system of claim 1, wherein the faceplate assembly has a convex contour.

3. The ostomy pouch system of claim 1, wherein the ostomy pouch system is a two-piece ostomy pouch system including a pouch assembly and the faceplate assembly; wherein the pouch assembly includes the pouch and a first coupling ring attached on the pouch; wherein the faceplate assembly includes a second coupling ring; wherein the first coupling ring and the second coupling ring are configured to engage together to attach the pouch assembly to the faceplate assembly.

4. The ostomy pouch system of claim 3, wherein the faceplate assembly further includes a convex insert, wherein the convex insert includes a first surface having a convexity and a second surface; wherein the convex insert is attached to the faceplate; wherein the stoma collar is arranged between the faceplate and the convex insert; wherein the stoma collar includes a collar portion that protrudes from the faceplate assembly; wherein both the convexity of the convex insert and the collar protrude in a same direction toward a stoma when the faceplate assembly is positioned proximate the stoma for attachment to a user.

5. The ostomy pouch system of claim 4, wherein the convex insert includes an inner convex portion, a base, and an inner wall defined by the inner convex portion; wherein the stoma collar includes a collar and a convex base; wherein the inner convex portion and the convex base have a same convex contour; wherein the convex base sits on the inner convex portion, and the faceplate and the skin barrier are disposed over the convex base, such that the convex base is sandwiched between the inner convex portion and the faceplate; wherein the inner convex portion defines a convexity of the faceplate assembly.

6. The ostomy pouch system of claim 4, wherein the second coupling ring is attached to the second surface of the convex insert.

7. The ostomy pouch system of claim 5, wherein the stoma collar further includes an annular tab formed on an inner surface about an intersection between the collar and the convex base; wherein the stoma collar is arranged on the convex insert such that the annular tab butts against the inner wall of the convex insert.

8. The ostomy pouch system of claim 1, wherein the ostomy pouch system is a one-piece ostomy pouch system, wherein the pouch is permanently attached to the faceplate assembly; wherein the faceplate assembly further includes a convex insert, the convex insert including an inlet opening; wherein the stoma collar includes a collar and a base; wherein the base is arranged between the skin barrier and the faceplate; wherein the collar and the convex insert protrude in a same direction toward a stoma when the faceplate assembly is positioned proximate the stoma for attachment to a user.

9. The ostomy pouch system of claim 1, wherein the stoma collar is formed from a flexible material having an elastic memory, such that when a stoma is received through an inlet opening defined by the stoma collar, the stoma collar hugs the stoma and becomes inverted as the stoma enters through the inlet opening of the faceplate, wherein the inverted stoma collar applies sufficient pressure around the stoma to seal around the stoma without strangulating the stoma.

10. The ostomy pouch system of claim 1, wherein the stoma collar is formed from silicone.

11. The ostomy pouch system of claim 1, wherein the stoma collar is formed from a skin barrier material.

12. The ostomy pouch system of claim 11, wherein the stoma collar is formed from an extended wear skin barrier material.

* * * * *